US00PP27000P3

(12) United States Plant Patent
Jacobs

(10) Patent No.: US PP27,000 P3
(45) Date of Patent: Aug. 2, 2016

(54) ***CHRYSANTHEMUM* PLANT NAMED 'ZANMUZEST'**

(50) Latin Name: ***Chrysanthemum×morifolium* Ramat**
Varietal Denomination: Zanmuzest

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 14/544,363

(22) Filed: Dec. 30, 2014

(65) Prior Publication Data
US 2016/0192567 P1 Jun. 30, 2016

(51) Int. Cl.
*A01H 5/02* (2006.01)

(52) U.S. Cl.
USPC ..... Plt./290

(58) Field of Classification Search
USPC ..... Plt./290
CPC ..... A01H 5/0255; A01H 5/025
See application file for complete search history.

*Primary Examiner* — Kent L Bell
(74) *Attorney, Agent, or Firm* — Steptoe & Johnson LLP

(57) ABSTRACT

A *chrysanthemum* plant named 'Zanmuzest' characterized by its medium sized blooms with bronze ray florets and prolific branching; natural season flowering date September 22; blooming for a period of about 4 to 5 weeks.

3 Drawing Sheets

Botanical designation: *Chrysanthemum×morifolium* Ramat.

Cultivar denomination: 'Zanmuzest'.

RELATED CULTIVARS

This new plant cultivar 'Zanmuzest' is of the botanical classification *Chrysanthemum×morifolium* Ramat.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuzest'. 'Zanmuzest' is a product of a breeding and selection program for outdoor pot mums (garden mums) which had the objective of creating new cultivars with a double type inflorescence, a natural season flowering date around September 22, blooming for a period of about 4 to 5 weeks. 'Zanmuzest' is a seedling resulting from a cross of the female parent 24577 with the male parent 17159. Plants of the new cultivar 'Zanmuzest' differ from plants of the female parent in the following characteristics. (1) Ray-floret color. And (2) Natural season flowering date. (1) Ray-florets of the seedling are bronze colored, while those of the female parent are yellow-bronze. (2). Plants of the seedling flower two weeks later in the season than those of the female parent. Plants of the new cultivar 'Zanmuzest' differ from plants of the male parent in ray-floret color; the seedling have bronze colored ray-florets, while the male parent has dark bronze colored ray-florets.

The new and distinct cultivar was discovered and selected as a flowering plant by Henricus Cornelius Maria Jacobs on a cultivated field in Rijsenhout, The Netherlands in 2009. The first act of asexual production of 'Zanmuzest' was accomplished when vegetative cuttings from the initial selection in 2009 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
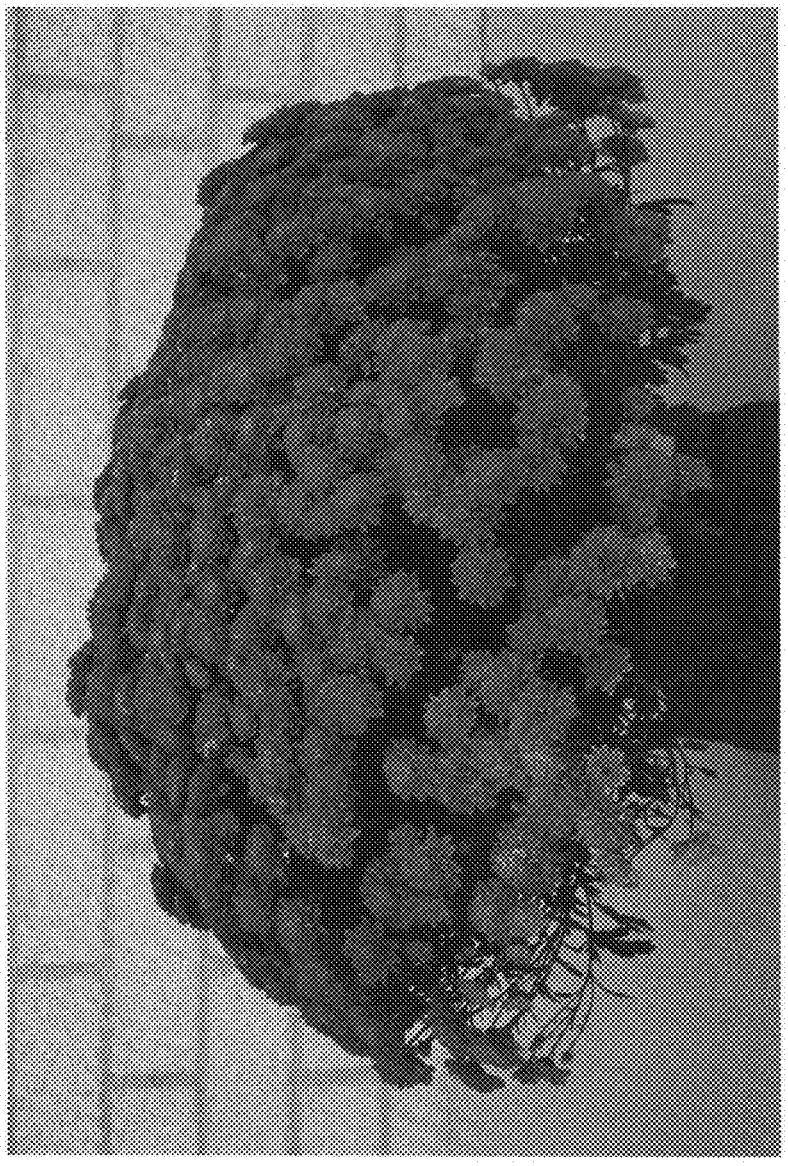
FIG. 1 shows a plant of the cultivar in full bloom.
Figure 2:
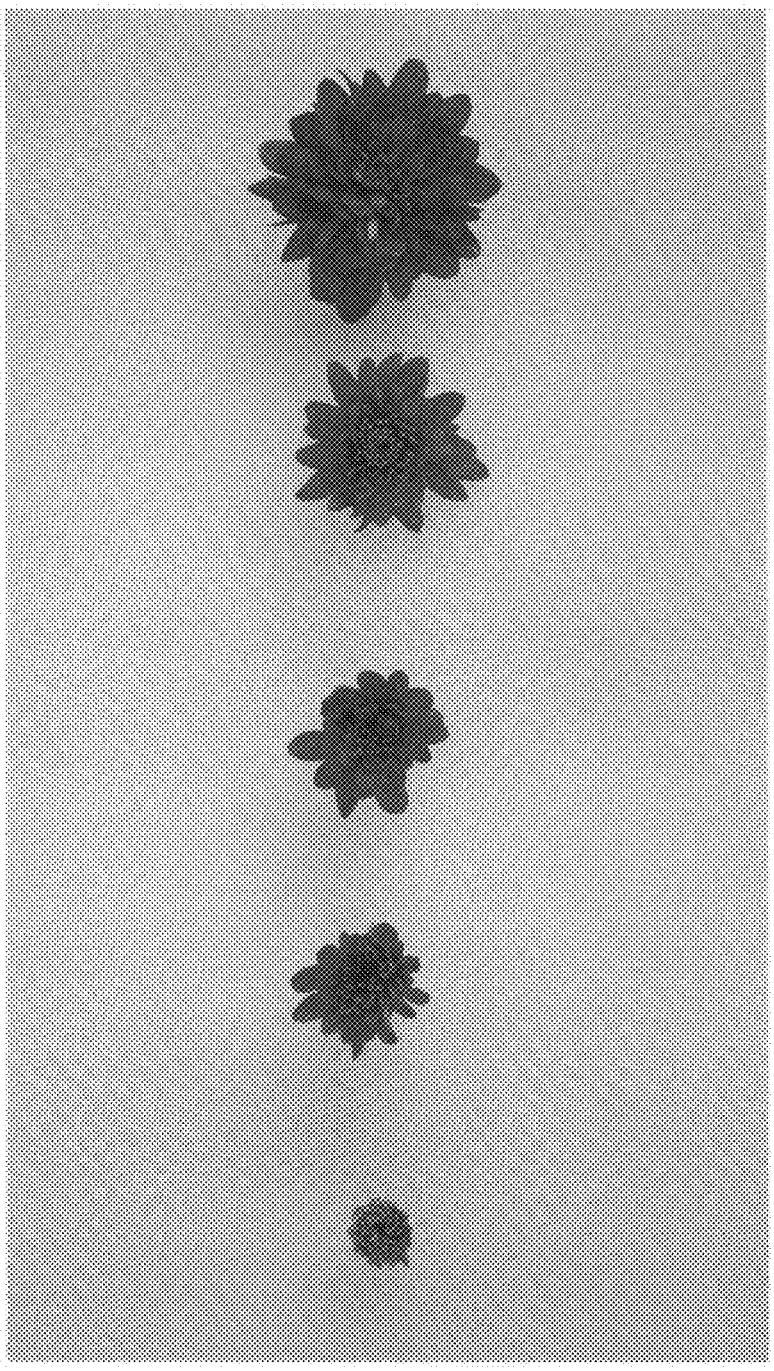
FIG. 2 shows the various stages of bloom of the new cultivar.
Figure 3:
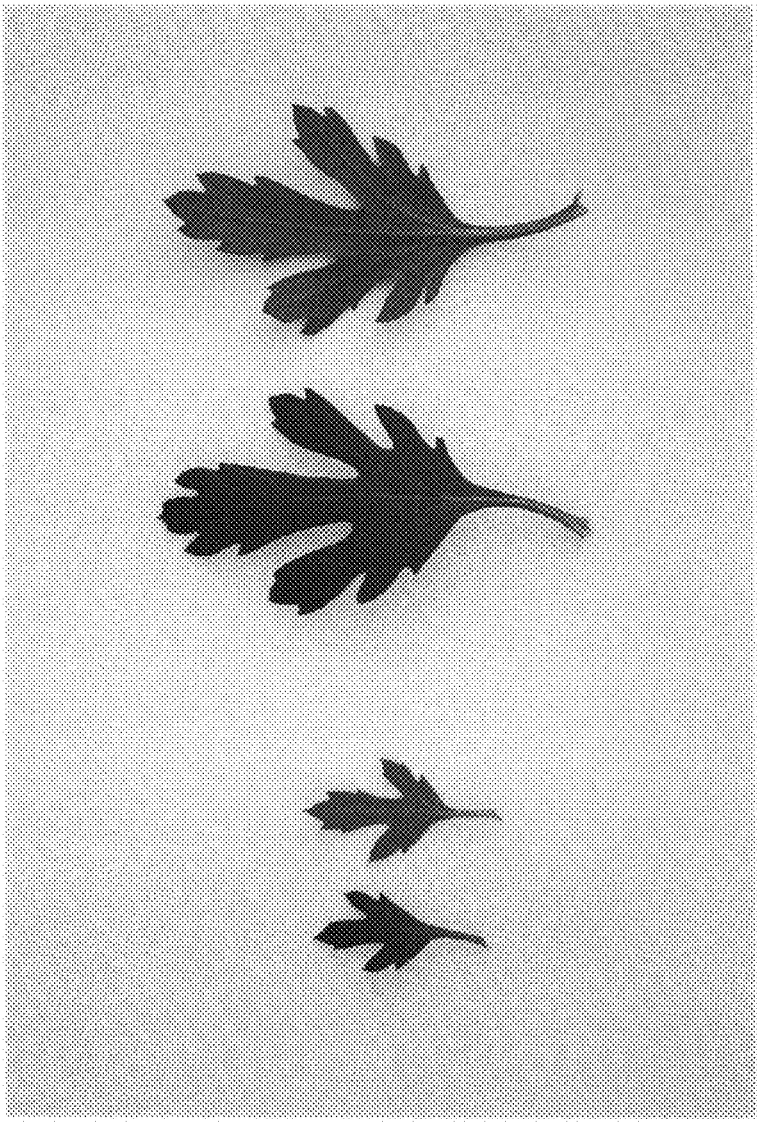
FIG. 3 shows the various stages of foliage of the new cultivar.

The observations and measurements were gathered from plants grown out door in Rijsenhout, The Netherlands, under natural day length and temperature and planted in week 25 in 2014, receiving drip irrigation. The natural blooming date of this crop was September 22. The average height of the plants was 30-35 cm. No growth retardants were used. No tests were done on disease or insect resistance or susceptibility. No tests were done on cold or drought tolerance. This new variety produces medium sized blooms with bronze ray florets blooming for a period of about 4 to 5 weeks.

From the cultivars known to inventor the most similar existing cultivar in comparison to 'Zanmuzest' is 'Zanmutomic' (U.S. Plant Pat. No. 21,183). When 'Zanmutomic' and 'Zanmuzest' are being compared the following difference is noticed: natural season flowering date. Plants of 'Zamutomic' flower earlier in the season than those of 'Zanmuzest'.

The following is a description of the plant and characteristics that distinguish 'Zanmuzest' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmuzest'

| | |
|---|---|
| **Bud** | |
| Size: | Small; cross-section 0.7-1 mm, height 5-7 mm |
| Shape: | Round |
| Texture: | Pubescent |
| Outside color: | Greyed-green 191A |
| **Phyllaries** | |
| Number: | 24, arranged in 3 rows |
| Shape: | Elliptic |
| Apex: | Acute |
| Base: | Truncate |
| Margin: | Entire |
| Color: | Upper side: Green 139B<br>Lower side: Greyed-green 191A |
| Length and width: | 4-5 mm; 1.5 mm |
| Texture: | Pubescent |
| **Inflorescences** | |
| Type: | Double |
| Height: | 1.8 cm |
| Diameter: | 5 cm |
| Peduncle length: | 4.5-7 cm |
| Peduncle color: | Greyed-green 191B |
| Peduncle diameter: | 1.5 mm |
| Peduncle texture: | Pubescent |
| Number per branch: | About. 5-7 inflorescences |
| Duration of flowering: | about 4 to 5 weeks |
| Seeds: | Produced in small quantities, ovate, Greyed-brown 199A, length 1.5 mm, diameter 0.5 mm |
| Fragrance: | Faint chrysanthemum odor |
| **Color inflorescences** | |
| Center of inflorescence (disc florets): | Immature stage: Greyed-orange 172A; Mature stage: Green-yellow 1B |
| Color of upper side of ray florets: | Yellow 4A at base to Greyed-Orange 171A at apex |
| Color of lower side of ray florets: | Greyed-Orange 162C at base to Greyed-Orange 173C at tip |
| Tonality from distance: | A garden mum with bronze blooms |
| Color of ray florets after aging of the plant: | Greyed-orange 171D |
| **Ray florets** | |
| Texture: | Upper and lower side smooth |
| Number: | 130-140 |
| Shape: | elliptic |
| Apex: | Pointed to dentate |
| Base: | Attenuate |
| Cross-section: | Flat |
| Longitudinal axis: | Straight |
| Length of corolla tube: | 2-3 mm |
| Ray floret margin: | Entire |
| Ray floret length: | 1.2-2.5 cm |
| Ray floret width: | 2-6 mm |
| Ratio length/width: | Medium |
| **Disc florets** | |
| Disc diameter: | 1-2 mm |
| Distribution of disc florets: | Few, only visible in mature stage of inflorescence |
| Shape: | Funnels shaped |
| Color: | Yellow-Green 145C at base to Green-Yellow 1B at apex |
| Length: | 3 mm |
| Diameter: | 1 mm |

TABLE 1-continued

Botanical Description of *Chrysanthemum* × *morifolium* Ramat. 'Zanmuzest'

| | |
|---|---|
| **Receptacle** | |
| Color: | Yellow-green 145D |
| Shape: | Domed raised |
| Height: | 4 mm |
| Diameter: | 2.8 mm |
| **Reproductive Organs** | |
| Androecium: | Present on only disc florets |
| Stamen length: | 3 mm |
| Stamen color: | Yellow-green 144A |
| Anther color: | Yellow 2A |
| Pollen: | Scarce |
| Pollen color: | Yellow 12A |
| Gynoecium: | Present on both ray and disc florets |
| Style color: | Yellow-green 154C |
| Style length: | 4 mm |
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Vigorous |
| Height: | 30-35 cm |
| Width: | 60-65 cm |
| Stem color: | Greyed-brown 199A |
| Stem strength: | Not strong |
| Stem brittleness: | Brittle |
| Stem anthocyanin coloration: | absent |
| Internode length: | 1-2.5 cm |
| Length of lateral branch: | From top to bottom 21-23 cm |
| Lateral branch color: | Green 138 A |
| Lateral branch, attachment: | Weak |
| Lateral branch diameter: | 2 mm |
| Branching (average number of lateral branches): | Prolific with 8 breaks after pinching |
| Natural season blooming date: | September 22 (week 39) |
| **Foliage** | |
| Leaf color: | Upper side: Green 137A<br>Lower side: Green 137B |
| Color midvein: | Upper side: Yellow-green 147D<br>Lower side: Yellow-green 148D |
| Size: | Small; length 3-6.5 cm, width 1.7-3 cm |
| Quantity (number per lateral branches): | 10-12 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Truncate to attenuate |
| Apex: | Mucronulate |
| Petiole length: | 0.8-1.5 cm |
| Petiole diameter: | 2 mm |
| Petiole color: | Yellow-green 147D |

TABLE 2

Differences with the comparison variety, when grown under identical conditions

| | 'Zanmuzest' | 'Zanmutomic' |
|---|---|---|
| Natural season flowering date | Week 39 | Week 37 |

I claim:

1. A new and distinct *chrysanthemum* plant named 'Zanmuzest' as described and illustrated.

* * * * *